(12) United States Patent
Ries et al.

(10) Patent No.: US 9,889,310 B2
(45) Date of Patent: Feb. 13, 2018

(54) SUTURE LOOP WITH COVER AND STRATEGIC PLACEMENT OF SUTURE POINTS

(71) Applicant: Medtronic, Inc., Minneapolis, MN (US)

(72) Inventors: Andrew J Ries, Lino Lakes, MN (US); Richard P Nelson, Hudson, WI (US); Kamal Deep Mothilal, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/338,815

(22) Filed: Jul. 23, 2014

(65) Prior Publication Data

US 2016/0023012 A1 Jan. 28, 2016

(51) Int. Cl.
| | | |
|---|---|---|
| *A61N 1/39* | (2006.01) | |
| *A61N 1/375* | (2006.01) | |
| *A61N 1/372* | (2006.01) | |
| *A61N 1/05* | (2006.01) | |

(52) U.S. Cl.
CPC ........... *A61N 1/3968* (2013.01); *A61N 1/372* (2013.01); *A61N 1/375* (2013.01); *A61N 1/057* (2013.01); *A61N 1/0558* (2013.01); *A61N 2001/0582* (2013.01)

(58) Field of Classification Search
CPC ............................. A61N 1/3968; A61N 1/3956
USPC ........................................................... 607/36
See application file for complete search history.

(56) References Cited

U.S. PATENT DOCUMENTS

| | | | |
|---|---|---|---|
| 5,203,787 A * | 4/1993 | Noblitt | A61B 17/0401 411/460 |
| 5,372,604 A | 12/1994 | Trott | |
| 5,895,414 A | 4/1999 | Sanchez-Zambrano | |
| 6,592,571 B1 | 7/2003 | Verbeek et al. | |
| 8,718,774 B2 | 5/2014 | Knipfer | |
| 2006/0200200 A1* | 9/2006 | Malinowski | A61N 1/025 607/2 |
| 2010/0274195 A1 | 10/2010 | Eichers | |
| 2010/0274309 A1 | 10/2010 | Knipfer et al. | |
| 2010/0280531 A1* | 11/2010 | Kalpin | A61M 5/14276 606/148 |
| 2010/0305627 A1 | 12/2010 | Anderson | |

(Continued)

FOREIGN PATENT DOCUMENTS

WO 2006126201 A2 11/2006

OTHER PUBLICATIONS

Internet Forum posting "Luggage Compartment Part 2—The Forward Lashing Hooks" (E90Post.com, http://www.e90post.com/forums/showthread.php?t=419180, posts dated Aug. 12, 2010).*

(Continued)

*Primary Examiner* — Carl H Layno
*Assistant Examiner* — Erin M Piateski

(57) ABSTRACT

An implantable medical device housing has an outer surface and an inner surface that defines an interior cavity. A wire is coupled to the housing outer surface. The wire wholly defines an open aperture for receiving a fixation member. The wire includes a first wire end, a second wire end, and an annular loop between the first and second ends. A cover extends over at least the first end and the second end of the wire.

23 Claims, 4 Drawing Sheets

(56) References Cited

U.S. PATENT DOCUMENTS

2012/0095478 A1    4/2012  Wang
2013/0085513 A1*   4/2013  North .................... A61N 1/375
                                                        606/148

OTHER PUBLICATIONS

Mr. Lock House Key Cap (http://www.mrlock.com/lucky-line-house-key-cap-red-25-per-bag-16270, visited Mar. 20, 2017).*
Google search result for "Key cap", sorted by date, saved Mar. 14, 2017.*
Google image result for Mr. Lock Key Cap, saved Mar. 14, 2017.*

* cited by examiner

SUTURE LOOP WITH COVER AND STRATEGIC PLACEMENT OF SUTURE POINTS

TECHNICAL FIELD

The disclosure relates generally to implantable medical devices and, in particular, to an implantable medical device housing having a suture loop for stabilizing device placement.

BACKGROUND

Numerous types of implantable medical devices (IMDs) are available for monitoring a patient and/or delivering automatic therapies, such as ECG monitors, cardiac monitors, pacemakers, defibrillators, drug delivery pumps, neurostimulators and the like. A general design goal in the manufacture of IMDs is to provide a smooth, rounded shape and minimal size of the IMD to promote patient comfort. Additionally, it is desirable to minimize the cost and complexity of manufacturing steps used in producing IMDs.

The outer housing of the IMD encloses electronics that perform the various IMD functions such as acquiring and analyzing physiological signals, automatically delivering therapies, and wirelessly communicating with an external programmer or other device. The housing reliably shields internal electronics that could be damaged or malfunction if exposed to body fluids.

In some medical applications, the IMD placement at an implant site or "pocket" is critical to proper functioning for sensing physiological signals and/or delivering effective therapies. For example, an implantable cardioverter defibrillator (ICD) that delivers defibrillation shocks to the heart using subcutaneous electrodes and the ICD housing or can electrode may be implanted to achieve a desired shock vector through the heart. Migration of the ICD may compromise the efficacy of the defibrillation shocks or increase the shock energy required to effectively defibrillate the heart.

DETAILED DESCRIPTION

A housing for an IMD and associated method of manufacture as disclosed herein may be implemented in a variety of implantable medical devices. The housing may be a metallic material such as titanium, titanium alloy, stainless steel, stainless steel alloy, or other metal or metal alloy. The illustrative examples described herein relate to a subcutaneous ICD having a housing electrode that is a portion of the metallic, electrically conductive housing. In other examples, however, the IMD housing may be a ceramic, glass or polymeric material and is not limited to a metallic housing. Furthermore, the housing and method of manufacture as disclosed herein are not limited to a particular type or size of IMD.

Figure 1:
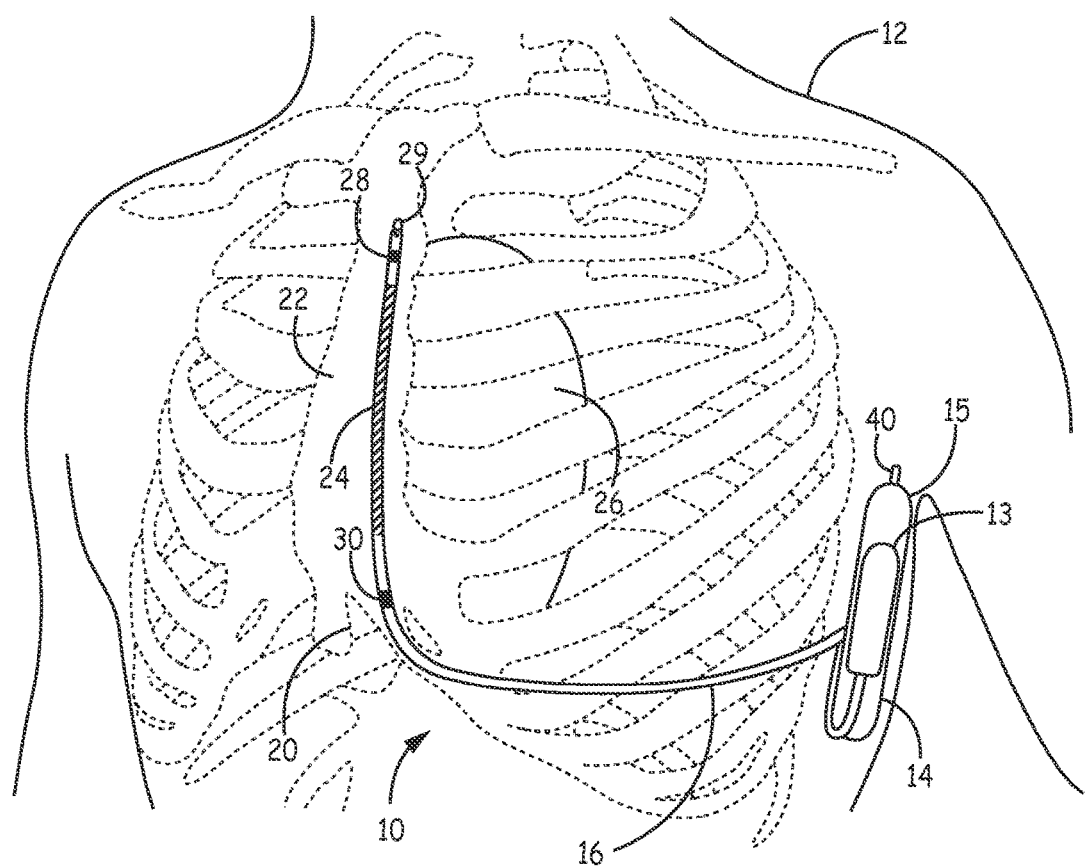
FIG. 1 is a conceptual diagram illustrating an implantable medical device (IMD) system 10.

FIG. 1 is a conceptual diagram illustrating an implantable medical device (IMD) system 10 that may be used to sense cardiac electrical signals in patient 12 and provide therapy to heart 26. IMD system 10 includes an ICD 14 coupled to an extravascular lead 16. ICD 14 is shown implanted subcutaneously on the left side of patient 12.

ICD 14 includes a housing 15 that forms a hermetic seal that protects components within ICD 14. Housing 15 may enclose one or more components, including processors, memories, transmitters, receivers, sensors, sensing circuitry, therapy circuitry and other appropriate components (often referred to herein as modules). The housing 15 of ICD 14 may be formed of a conductive material, such as titanium or other biocompatible conductive material or a combination of conductive and non-conductive materials. In some instances, the housing 15 functions as an electrode (sometimes referred to as a housing electrode or can electrode) that is used in combination with one of electrodes 24, 28 and 30 to deliver a therapy to heart 26 or to sense electrical activity of heart 26.

ICD 14 may include a connector assembly 13 (sometimes referred to as a connector block or header) for receiving a proximal connector (not illustrated) of lead 16. Connector assembly 13 includes electrical feedthroughs through which electrical connections are made between conductors within defibrillation lead 16 and electronic components included within the housing.

Defibrillation lead 16, which is connected to ICD 14, extends medially from ICD 14 toward sternum 22 and xiphoid process 20 of patient 12. At a location near xiphoid process 20 defibrillation lead 16 bends or turns and extends subcutaneously superior, substantially parallel to sternum 22 in the example shown. Lead 16 may extend in other subcutaneous, substernal or intrathoracic locations in other examples.

Defibrillation lead 16 includes a defibrillation electrode 24, which may be an elongated coil electrode and a pair of a sensing electrodes 28 and 30. Defibrillation lead 16 may also include an attachment feature 29 at or toward the distal end of lead 16. Attachment feature 29 may be useful to aid in implantation of lead 16 and/or for securing lead 16 to a desired implant location.

Defibrillation lead 16 is placed along sternum 22 such that a therapy vector between defibrillation electrode 24 and a second electrode that is a portion of the housing 15 of ICD 14 is substantially across one or both ventricles of heart 26. The therapy vector may, in one example, be viewed as a line that extends from a point on the defibrillation electrode 24 to a point on the housing 15 (or can electrode) of ICD 14. In another example, defibrillation lead 16 may be placed along sternum 22 such that a therapy vector between defibrillation electrode 24 and housing 15 of ICD 14 (or other electrode) is substantially across an atrium of heart 26. In this case, system 10 may be used to provide atrial therapies, such as therapies to treat atrial fibrillation.

In order to maintain a desired therapy vector, a suture ring 40 is coupled to the IMD housing 15 along a peripheral side corresponding to a top side (or cephalic side in the orientation shown) of the IMD 14 when implanted in a desired configuration relative to heart 26. Suture ring 40 reduces the likelihood of migration of IMD 14 and maintains the relative positions of IMD 14, electrodes 24, 28 and 30, and heart 26.

Although ICD 14 is illustrated as being implanted near a midaxillary line of patient 12, ICD 14 may also be implanted at other subcutaneous locations on patient 12, such as further posterior on the torso toward the posterior axillary line, further anterior on the torso toward the anterior axillary line, in a pectoral region, or at other locations of patient 12. In instances in which ICD 14 is implanted pectorally, lead 16 would follow a different path, e.g., across the upper chest area and inferior along sternum 22. When the ICD 14 is implanted in the pectoral region, the system 10 may include a second lead including a defibrillation electrode that extends along the left side of the patient such that the defibrillation electrode of the second lead is located along the left side of the patient to function as an anode or cathode of the therapy vector for defibrillating heart 26. It is recognized that various implant configurations may be conceived or considered most optimal for a particular medical application or patient. A suture ring 40 is provided along one or more sides of housing 15, i.e. along one or more median or laterally offset axes of housing 15, as needed to prevent migration along a gravitational axis. As further described below, the gravitational axis may change with changes in patient posture or body position, requiring more than one suture ring along more than one side of housing 15. Migration prevented or minimized by suture ring 40 includes lateral shifting as well a rotation of housing 15.

ICD 14 may sense electrical activity of heart 26 via one or more sensing vectors that include combinations of electrodes 28 and 30 and a housing 15 or can electrode of ICD 14. For example, ICD 14 may obtain electrical signals sensed using a sensing vector between electrodes 28 and 30, between electrode 28 and the conductive housing 15, between electrode 30 and housing 15, or any combination thereof. ICD 14 may analyze the sensed electrical signals to detect tachycardia, such as ventricular tachycardia or ventricular fibrillation, and in response to detecting tachycardia may generate and deliver an electrical therapy to heart 26. For example, ICD 14 may deliver one or more defibrillation shocks via a therapy vector that includes defibrillation electrode 24 and the housing 15.

The example ICD 14 illustrated in FIG. 1 is illustrative in nature and should not be considered limiting of an implantable medical device including a suture ring 40 as described in this disclosure. Other examples of ICDs that may include a suture ring as disclosed herein are generally described in U.S. Pat. No. 7,904,153 (Greenhut, et al.) and U.S. Pat. No. 7,383,085 (Olson, et al.), all of which patents are hereby incorporated herein by reference in their entirety.

Furthermore, other IMDs such as, and without limitation, pacemakers, neurostimulators, sensors, ECG or other cardiac monitors, or drug or fluid delivery pumps may include a suture ring as disclosed herein. Migration of an IMD is undesirable in a number of medical applications besides the example presented herein for reliably maintaining a defibrillation vector between a lead-based electrode and the ICD housing electrode. Minimal IMD migration may be desirable in cases of therapy delivery as well as physiological sensing that involve a housing based electrode, sensor, or other therapy delivery or sensing means such as a port or conduit. For example, a sensing vector between electrodes that include an IMD housing-based electrode for sensing electrophysiological signals, such as an electrocardiogram (ECG), may be altered by IMD migration, causing an undesirable change in the electrical signal. A measurement volume in tissue adjacent to other types of IMD housing-based physiological sensors, such as an optical sensor, may be altered if the IMD shifts or rotates. Migration of the IMD housing, and thus migration of electrodes and/or other physiological sensors present along the IMD housing, could confound measurements taken from a sensed signal. Furthermore, minimal IMD migration may be desired for promoting patient comfort. Accordingly, the illustrative embodiments presented herein are not intended to limit the type of IMD which may implement a suture ring as presently disclosed.

Figure 2A:
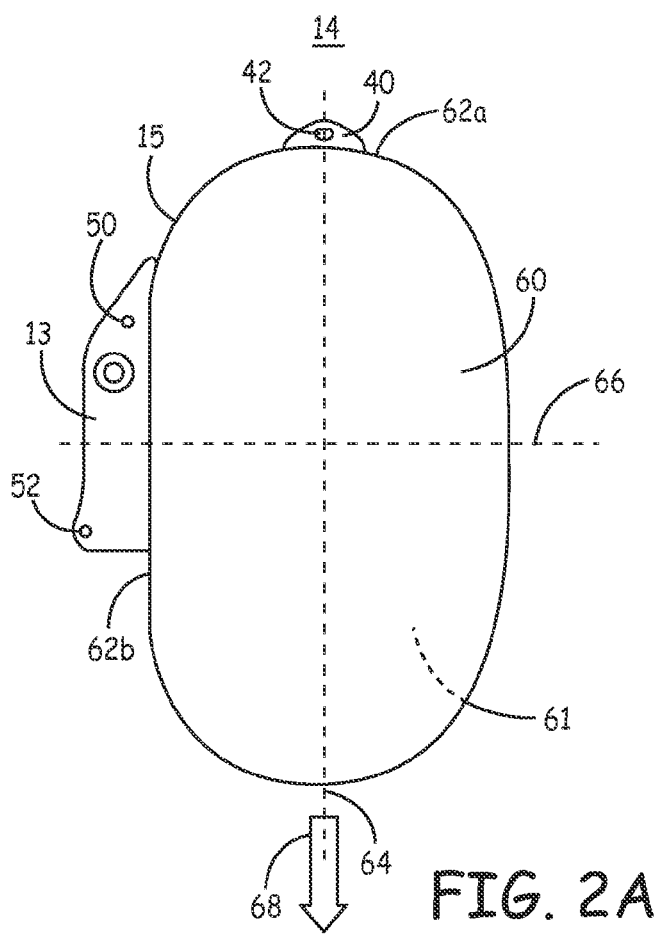
FIG. 2A is a conceptual view of the ICD of FIG. 1 depicting a suture ring.

FIG. 2A is a conceptual view of ICD 14 depicting suture ring 40. ICD 14 has a major side 60 separated from a second major side 61 (not visible in the view of FIG. 2A) separated by a peripheral side 62, including a first peripheral side 62*a* and a second peripheral side 62*b*. ICD 14 has a major axis 64 and a minor axis 66. When ICD 14 is implanted in the orientation shown in FIG. 1, the major axis 64 is aligned with the direction of the gravitational axis as indicated by arrow 68 when the patient 12 is in a standing or upright position. Suture ring 40 is directly coupled to the housing peripheral side 62 such that it is aligned with the gravitational axis direction 68 to counteract gravitational pull that may cause ICD migration when the patient is in an upright position.

Suture ring 40 defines an aperture 42 for receiving an elongated fixation member, such as but not limited to a suture or staple (not shown). In some examples, aperture 42 is centered along an axis that extends through a center of gravity of ICD 14. However, being centered along a gravitational axis of ICD 14 is not required in some embodiments, particularly if other suture rings or anchoring points of the ICD are provided. For example, ICD connector block 13 is shown to include two suture through-holes 50 and 52 formed in connector block 13. Center axes of through holes 50 and 52 extend in parallel to minor axis 66, i.e. orthogonal to major axis 64 and the gravitational axis direction 68 when the patient is in an upright or standing position. When sutures are placed through aperture 42 and through-holes 50 and 52, rotation of ICD 14 and lateral migration along major axis 64 and along minor axis 66 are minimized or prevented. For example, if anchoring sutures are placed only in connector block suture through-holes 50 and 52, rotation of ICD 14 may occur due to the direction 68 gravitational pull along the gravitation axis of the ICD 14. An additional suture through suture ring 42 will reduce the likelihood of rotation.

It is recognized that one or more suture rings 40 may be coupled to housing 15 along any portion of peripheral side 62 between major sides 60 and 62. For example, another suture ring may be positioned along the opposite end of peripheral side 62 pointing in the caudal direction when the patient is standing or upright, opposite suture ring 40. Additional suture rings may be provided to limit rotation of ICD 14 that may occur if anchored only at a single point or along a single side of ICD 14.

Figure 2B:
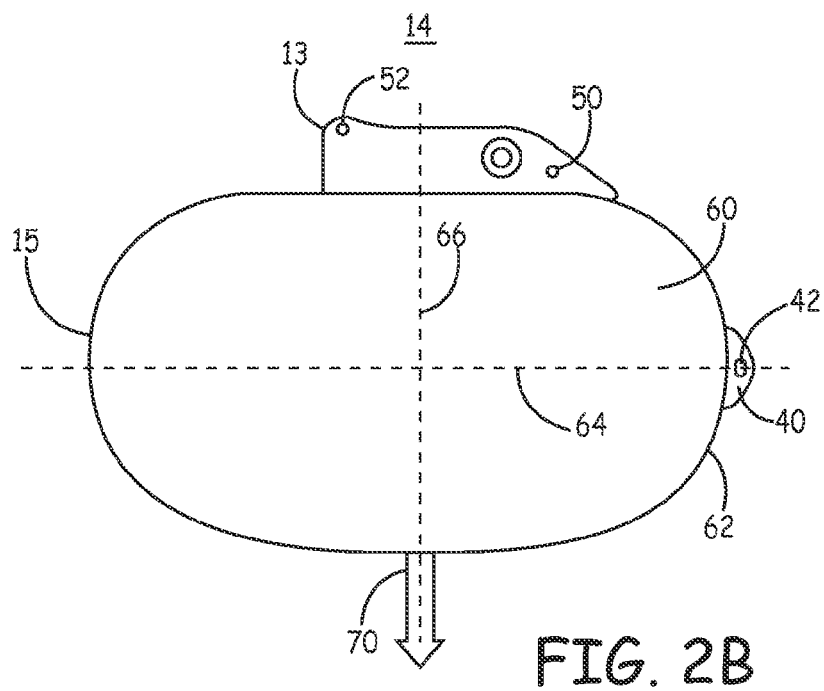
FIG. 2B shows the ICD of FIG. 2A in a horizontal orientation representing the gravitational axis direction when the patient is lying down.

FIG. 2B depicts ICD 14 in a horizontal orientation representing the gravitational axis direction (arrow 70) when the patient is lying down. In this orientation, sutures placed in through-holes 50 and 52 reduce migration along minor axis 66 due to gravitational forces when the patient is lying down. A suture through suture ring aperture 42 prevents rotational motion of ICD 14.

Figure 3A:
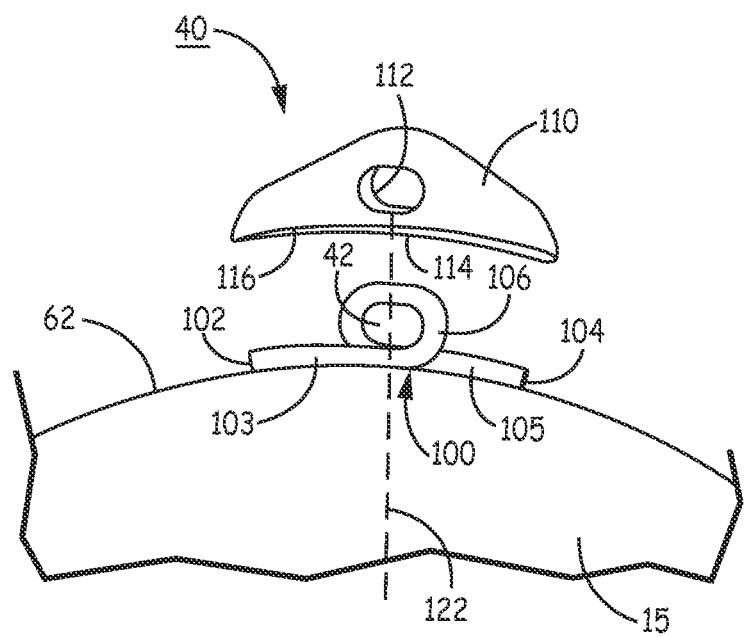
FIGS. 3A and 3B are enlarged views of the suture ring shown in FIG. 2A.
Figure 3B:
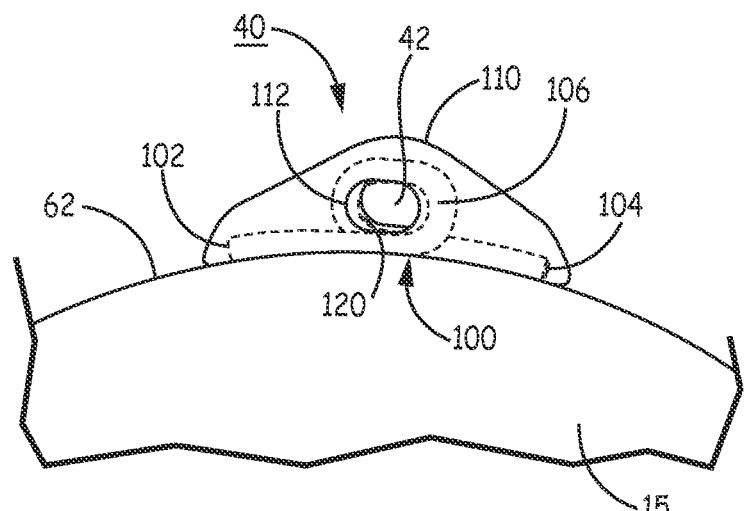

FIGS. 3A and 3B are enlarged views of suture ring 40 unassembled (FIG. 3A) and assembled (FIG. 3B) with a cover. Suture ring 40 is a covered suture ring including a wire 100 and a rounded, smooth cover 110. Wire 100 may be a round, metal wire that is welded directly to housing 15. Wire 100 may be, without limitation, titanium, stainless steel, niobium or alloys thereof or other biocompatible metal or metal alloy. In other embodiments, wire 100 may be formed from a polymer such as polyether ether ketone (PEEK), poly-ether based thermoplastic polyurethane (e.g. TECOTHANE®) or other polyurethane, elastane, or other biocompatible polymer wire that may be adhesively coupled to housing 15. It is recognized that wire 100 may be single round wire or a stranded, braided, or cabled wire. The material selected for wire 100 may depend on the material that is used for housing 15. For example, if housing 15 is a polymeric housing, a polymer wire may be used in suture ring 40 whereas if housing 15 is glass, ceramic or metal, a metallic wire 100 may be welded, brazed, fusion bonded or adhesively coupled to housing 16.

Wire 100 includes legs 103 and 105 extending to opposing wire ends 102 and 104, respectively, and an annular loop 106 between wire ends 102 and 104. Wire 100 may be coupled directly to housing 15 along legs 103 and 105 and ends 102, 104. Wire loop 106 defines aperture 42 for receiving an elongated fixation member such as a suture or staple. Annular loop 106 has a center axis 120 that may be aligned with a gravitational axis of the implantable medical device associated with a first patient position, for example a standing or upright position as generally depicted in FIGS. 1 and 2A. Center axis 122 may be orthogonal to a center axis of a through-hole 50 or 52 included in the connector block 13 as shown in FIG. 2A.

Annular loop 106 is shown generally "0" shaped in the examples presented herein. It is recognized that annular loop 106 may be generally elliptical, circular, oval, D-shaped, or other ring shape as long as the wire 100 wholly defines and fully circumscribes aperture 42. By providing a loop 106 that wholly defines aperture 42 rather than only a portion of aperture 42, a suture or other elongated fixation member is unable to slip out of aperture 42. The continuous inner diameter 120 (FIG. 3B) defined by the annular loop 106 prevents the suture from becoming wedged along a corner or edge between the wire 100 and the housing 15 which may wear the suture over time or even cut the suture.

For example, a U-shaped wire may be attached to housing 15 having legs extending outward from the "U" shape along peripheral side 62. In this configuration, a suture placed in the aperture defined by the U-shaped wire along three sides and the housing surface on the fourth side may slip into a corner between the housing and the wire. In this position, the suture may be more likely to become worn or severed than if the suture is held within the annular loop 106 wholly defined by wire 100.

Legs 103 and 105 extend in parallel to each other from the annular loop 106 to the respective opposing ends 102 and 104. Legs 103 and 105 are shown to extend in a non-overlapping, non-twisting manner such that the entirety of legs 103 and 105 extend in parallel contact with each other toward opposing wire ends 102 and 104, which extend in opposite directions from each other, i.e. 180 degrees from each other. The parallel contacting legs 103 and 105 define a portion of the annular loop 106 such that aperture 42 is wholly defined by wire 100. The parallel legs 103 and 105 provide a relatively large surface area for interfacing with housing 15 and for welding or bonding wire 100 directly to housing 15.

In other examples, wire ends 102 and 104 may extend in different directions that are not necessarily 180 degrees apart. For example, one or both of legs 103 and 105 may have a bend between annular loop 106 and respective end 102 or 104 that directs the ends 102 and 104 away from each other at a different angle than 180 degrees. For instance, ends 102 and 104 may extend 90 degrees relative to each other. In other examples, ends 102 and 104 may be directed in the same direction generally parallel to each other by including one or more bends in legs 103 and 105 in addition to annular loop 106. In each of these examples, the legs 103 and 105 may extend in parallel between annular loop 106 and respective ends 102 and 104 in a non-overlapping, non-twisting manner before bending in a non-parallel direction.

Suture ring 40 includes a cover 110 having a smooth, rounded contour. Cover 110 may be a molded plastic component that provides smooth rounded edges and corners to promote patient comfort. In various examples, cover 110 may be molded polyurethane, silicone, PEEK, liquid crystal polymer (LCP) or other biocompatible, biostable polymer material. Cover 110 defines an aperture opening 112 that becomes aligned with annular loop 106 defining aperture 42. Cover 110 has an open slot 114 for receiving wire 100 along a cover bottom side 116 that interfaces with the peripheral side 62 of housing 15. Cover 110 may have an interference fit with wire 100 to secure cover 110 over wire 100. Additionally or alternatively, a medical grade adhesive may be applied to cover 110 along bottom side 116 and/or along aperture opening 112 to seal cover 110 to wire 100 and/or housing 15.

The inner diameter 120 of annular loop 106 is exposed along aperture opening 112 in some examples. An exposed inner diameter of loop 106 allows the suture or other elongated fixation member extending through aperture 42 to engage with wire 100 directly. Cover 110 may be made of a lower durometer material than wire 100 to promote patient comfort. A tightly secured suture may cut into a relatively softer material of cover 110 over time. Accordingly, it may be desirable to provide exposure of at least a portion of the inner diameter 120 of loop 106 through cover 110 so that wire 100 engages directly with the suture at the point of greatest tension or pressure between suture ring 40 and the suture.

Cover 110 is shown having a generally trapezoidal shape in FIGS. 3A and 3B that covers all of wire 100 with the possible exception of at least a portion of loop inner diameter 120. It is recognized that cover 110 may be provided having other shapes that are generally rounded and smoothly contoured, i.e. without sharp corners or edges or tight radiuses. For example, cover 110 may be generally hemispherical, elliptical, etc.

Figure 4:
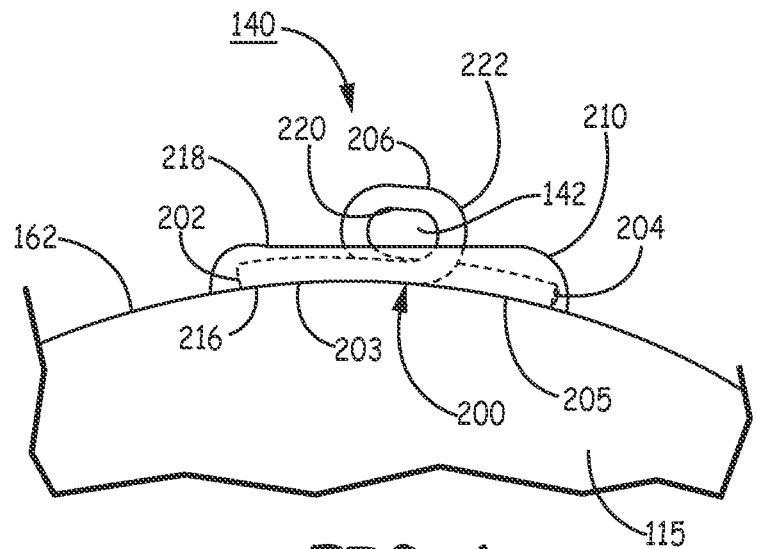
FIG. 4 is an enlarged, conceptual view of another example of a suture ring.

FIG. 4 is an enlarged, conceptual view of another example of a suture ring 140. In this example, wire 200 corresponds to wire 100 shown in FIG. 3A, having two opposing ends 202 and 204 and an intervening annular loop 206. In this example, however, cover 210 is a generally elongated and flat cover extending from just beyond wire end 102 to just beyond wire end 104. Annular loop 206 protrudes from a top side 218 of cover 210 so that at least a portion of both the inner diameter 220 and the outer diameter 222 of loop 206 are exposed. In this way, wire ends 202 and 204 are covered by the smooth, rounded contours of cover 210 to promote patient comfort, but annular loop 206 is exposed to engage with a tightly secured suture, staple or other elongated fixation member.

Cover 210 may be a pre-formed component including a slot along bottom side 216 for sliding over wire legs 203 and 205 and wire ends 202 and 204 and a slot along top side 218 for passing annular loop 206 through cover 210. Cover 210 may form an interference fit with wire 200 and/or may be stably secured to wire 200 and/or housing 15 using a medical grade adhesive.

Alternatively, cover 210 may be applied as a coating over portions of wire 100 before or after coupling wire 100 to housing 15. For example, cover 210 may be a medical grade adhesive, such as silicone or epoxy, that is applied and allowed to cure over at least wire ends 202 and 204. Wire ends 202, 204, portions of legs 203, 205 and a portion of annular loop 206 may be embedded within cover 210.

It is further contemplated that in some examples, when cover 210 is provided to enclose legs 203 and 205 and ends 202 and 204, the wire 200 may include a U-shape rather than a complete annular loop such that aperture 142 is defined by the wire 200 and the top side 218 of the cover 210.

Figure 5:
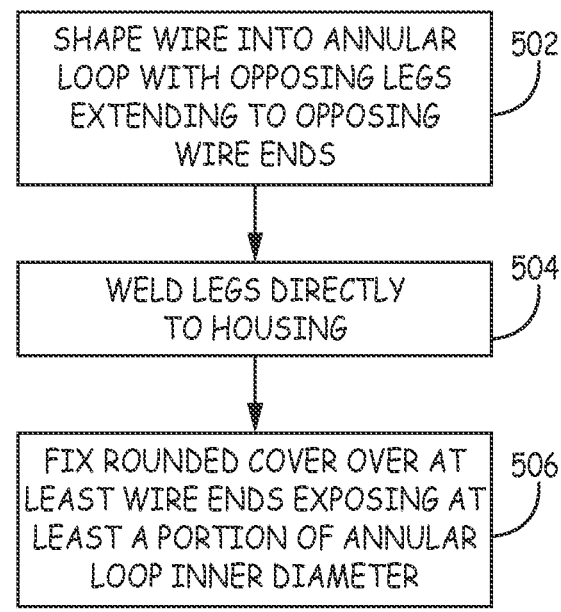
FIG. 5 is a flow chart of a manufacturing method for producing an IMD housing having a suture ring coupled directly to the housing according to one example.

FIG. 5 is a flow chart 500 of a manufacturing method for producing an IMD housing having a suture ring coupled directly to the housing according to one example. A round, metal wire is shaped into an annular loop having legs extending in parallel from the annular loop to opposing wire ends at block 502. Various shapes of the annular loop and variations of the direction of the legs and ends of the wire have been described above. A flat, square or other shaped wire may be used instead of a round wire, however, a round wire may promote greatest patient comfort and least likely to abrade or severe an elongated fixation member.

The wire legs and ends are welded directly to a metallic IMD housing at block 504. Alternative methods may be used to securely fix the wire to the IMD housing and coupling techniques used will depend on the material of the wire and the material of the IMD housing.

A rounded cover is fixed over at least the wire ends at block 506. Various examples of methods for fixing the cover over the wire and various possible shapes of the cover have been described above. At least the ends of the wire are covered by the rounded cover. At least a portion of the inner diameter of the annular loop is left exposed after fixing the cover over the wire ends.

Thus, an IMD housing having a suture ring has been presented in the foregoing description with reference to specific embodiments. The examples disclosed herein are for purposes of illustration. It is appreciated that various modifications to the referenced embodiments may be made without departing from the scope of the disclosure and the following claims.

The invention claimed is:

1. An implantable medical device, comprising:
a housing having an outer surface;
a wire coupled to the housing outer surface and wholly defining an open aperture for receiving a fixation member, the wire comprising a first wire end, a second wire end, and an annular loop defining the open aperture between the first and second wire ends, wherein the annular loop is centered along a gravitational axis through a center of gravity of the implantable medical device associated with a substantially upright patient position; and
a cover extending at least over the first wire end and the second wire end,
the wire further comprising a first leg and a second leg in parallel contact with each other defining a portion of the annular loop,
the first leg and the second leg each extending from the annular loop toward the first wire end and the second wire end, respectively,
the first and second legs in parallel contact defining a surface area that is coupled directly to the housing outer surface.

2. The device of claim 1, wherein the cover extends from the first wire end to the second wire end.

3. The device of claim 1, wherein the cover extends over at least a portion of the annular loop.

4. The device of claim 3, wherein the annular loop comprises an uncovered portion extending outward from the cover.

5. The device of claim 3, wherein the annular loop of the wire has an inner diameter that is at least partially exposed through the cover.

6. The device of claim 1, wherein the first and second wire ends are coupled directly to the housing.

7. The device of claim 1, wherein the wire comprises a first leg extending from the annular loop to the first wire end and a second leg extending from the annular loop to the second wire end, the first leg and the second leg extending in parallel to each other from the annular loop to the respective first wire end and second wire end.

8. The device of claim 1, wherein the housing further comprises a connector block having a through-hole for receiving a fixation member positioned along another axis orthogonal to the gravitational axis of the implantable medical device associated with the substantially upright patient position, the through-hole positioned such that the fixation member received by the through-hole provides an anchoring force to the implantable medical device that is substantially parallel to a gravitational axis of the implantable medical device associated with a substantially lying down patient position, the substantially lying down patient position substantially orthogonal to the substantially upright patient position.

9. The device of claim 1, wherein the housing comprises a first major side, a second major side, a first peripheral side extending from the first major side to the second major side and a long axis extending through the peripheral side,
the wire loop being coupled to the housing along the peripheral side.

10. The device of claim 9, wherein the housing comprises a second peripheral side extending between the first major side and the second major side and a short axis extending through the second peripheral side, the short axis orthogonal to the long axis, and
a connector block extending along the second peripheral side comprising a through-hole for receiving a fixation member.

11. The device of claim 1, wherein the cover comprises an aperture opening that is aligned with the annular loop defining the open aperture,
the annular loop having an inner diameter and an outer diameter,
the cover covering all of the wire except a portion of the inner diameter of the annular loop exposed along the aperture opening.

12. The device of claim 1, wherein the implantable medical device comprises only one aperture configured to receive the fixation member along a major axis of the implantable medical device, wherein the open aperture is the only one aperture.

13. An implantable medical device housing having an outer surface and an inner surface defining an interior cavity, comprising:
a wire coupled to the housing outer surface and wholly defining an open aperture for receiving a fixation member, the wire comprising a first wire end, a second wire end, and an annular loop defining the open aperture between the first and second ends, wherein the annular loop is centered along a gravitational axis through a center of gravity of the implantable medical device associated with a substantially upright patient position; and a cover extending at least over the first wire end and the second wire end, the wire further comprising a first leg and a second leg in parallel contact with each other defining a portion of the annular loop, the first leg and the second leg each extending from the annular loop toward the first wire end and the second wire end, respectively, the first and second legs in parallel contact defining a surface area that is coupled directly to the housing outer surface.

14. The housing of claim 13, wherein the cover extends from the first wire end to the second wire end.

15. The housing of claim 13, wherein the cover extends over at least a portion of the annular loop.

16. The housing of claim 15, wherein the annular loop comprises an uncovered portion extending outward from the cover.

17. The housing of claim 15, wherein the annular loop of the wire has an inner diameter that is at least partially exposed through the cover.

18. The housing of claim 13, wherein the first and second ends are coupled directly to the housing.

19. The housing of claim 13, wherein the wire comprises a first leg extending from the annular loop to the first wire end and a second leg extending from the annular loop to the second wire end, the first leg and the second leg extending in parallel to each other from the annular loop to the respective first wire end and second wire end.

20. The housing of claim 13, further comprising a connector block having a through-hole for receiving a fixation member positioned along another axis through the center of gravity orthogonal to the gravitational axis of the implantable medical device associated with the substantially upright patient position.

21. The housing of claim 13, further comprising a first major side, a second major side, a first peripheral side extending from the first major side to the second major side and a long axis extending through the peripheral side, the wire loop being coupled to the housing along the peripheral side.

22. The housing of claim 21, further comprising a second peripheral side extending between the first major side and the second major side and a short axis extending through the second peripheral side, the short axis orthogonal to the long axis, and a connector block extending along the second peripheral side comprising a through-hole for receiving a fixation member.

23. A method for manufacturing an implantable medical device housing, comprising:

shaping a wire into an annular loop wholly defining an open aperture and extending between a first wire end and a second wire end, wherein the annular loop is centered along a gravitational axis through a center of gravity of the implantable medical device associated with a substantially upright patient position;

coupling the wire directly to an outer surface of a housing of an implantable medical device; and fixing a cover over at least the first and second wire ends, wherein shaping the wire further comprises shaping a first leg and a second leg of the wire in parallel contact with each other defining a portion of the annular loop, the first leg and the second leg each extending from the annular loop toward the first wire end and the second wire end, respectively, wherein coupling the wire directly to the outer surface of the housing comprises coupling a surface area defined by the first and second legs in parallel contact directly to the housing outer surface.

* * * * *